(12) United States Patent
Falls

(10) Patent No.: US 6,514,254 B1
(45) Date of Patent: Feb. 4, 2003

(54) CLAMP DEVICE FOR ORTHOPEDIC EXTERNAL FIXATOR

(76) Inventor: John W. Falls, 3986 Loch Meade Dr., Memphis, TN (US) 38002

( * ) Notice: Subject to any disclaimer, the term of this patent is extended or adjusted under 35 U.S.C. 154(b) by 319 days.

(21) Appl. No.: 09/669,160

(22) Filed: Sep. 25, 2000

(51) Int. Cl.[7] .................... A61B 17/56; A61F 5/37; A61F 5/00
(52) U.S. Cl. .................... 606/54; 606/56; 602/27; 128/882
(58) Field of Search .............. 606/54, 53, 55, 606/56, 57, 58, 59; 602/27, 28, 26

(56) References Cited

U.S. PATENT DOCUMENTS

| | | | |
|---|---|---|---|
| 2,536,454 A | 1/1951 | McIntyre | 128/80 |
| 3,961,854 A | 6/1976 | Jaquet | 403/59 |
| 4,483,334 A | 11/1984 | Murray | 128/92 |
| 4,620,533 A | 11/1986 | Mears | 128/92 |
| 4,955,370 A | 9/1990 | Pettine | 128/80 |
| 5,277,699 A | 1/1994 | Williamson | 602/28 |
| 5,312,403 A * | 5/1994 | Frigg | 606/54 |
| 5,393,161 A * | 2/1995 | Mata et al. | 403/133 |
| 5,451,225 A * | 9/1995 | Ross et al. | 606/59 |
| 5,542,912 A | 8/1996 | Hess | 602/27 |
| 5,683,389 A * | 11/1997 | Orsak | 606/59 |
| 5,785,709 A * | 7/1998 | Kummer et al. | 606/56 |
| 5,860,423 A | 1/1999 | Thompson | 128/882 |

* cited by examiner

Primary Examiner—John J. Wilson
Assistant Examiner—Robyn Kieu Doan
(74) Attorney, Agent, or Firm—Walker, McKenzie & Walker PC

(57) ABSTRACT

A clamp device for use with an external skeletal fixator for being coupled to a patient's limb, and strap structure having a first end for being coupled to a patient's extremity and having a second end. The clamp device includes an elongated clamp rod; a first connection structure for adjustably attaching the clamp rod to a fixator rod of the external fixator; and a second connection structure for adjustably attaching the second end of the strap structure to the clamp rod.

10 Claims, 4 Drawing Sheets

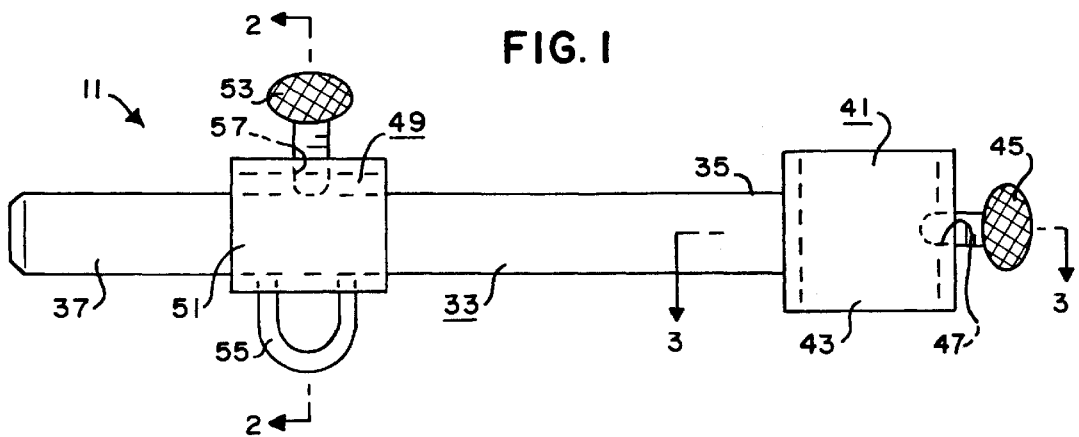
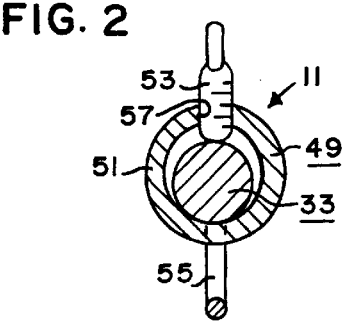
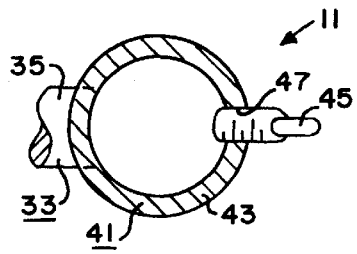
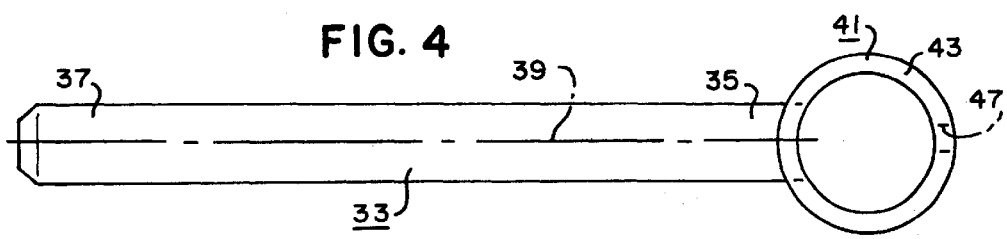
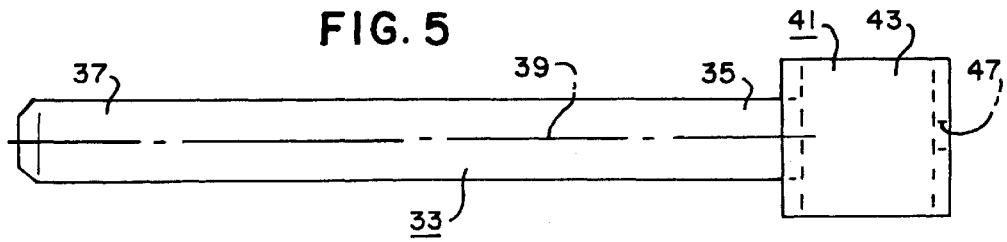

FIG. 14
FIG. 15
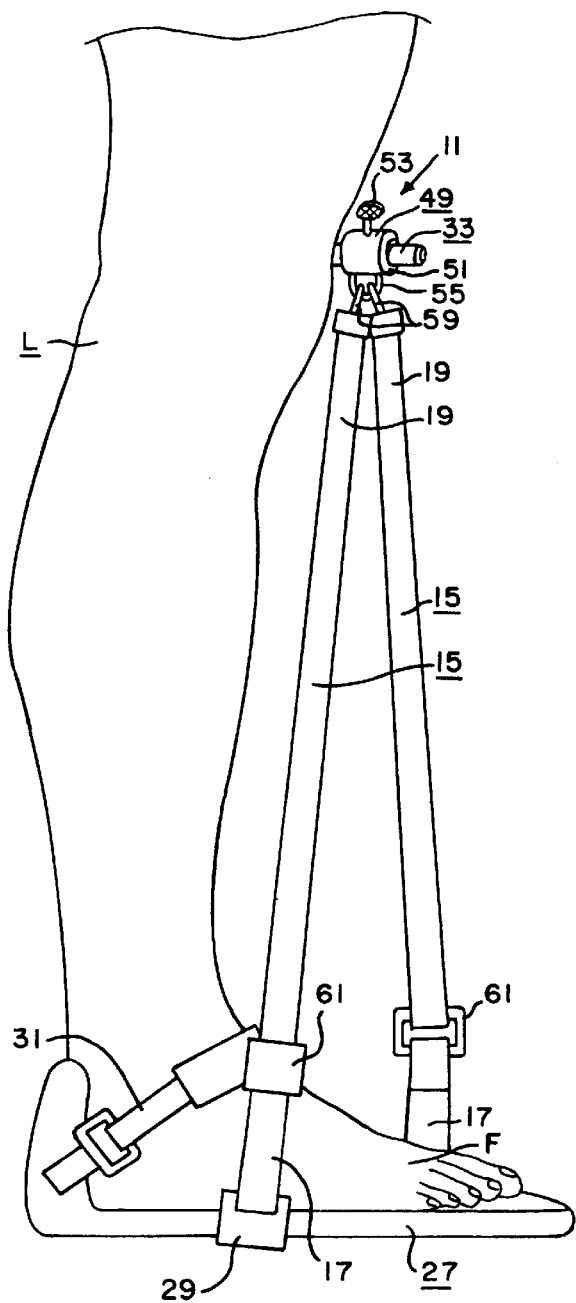
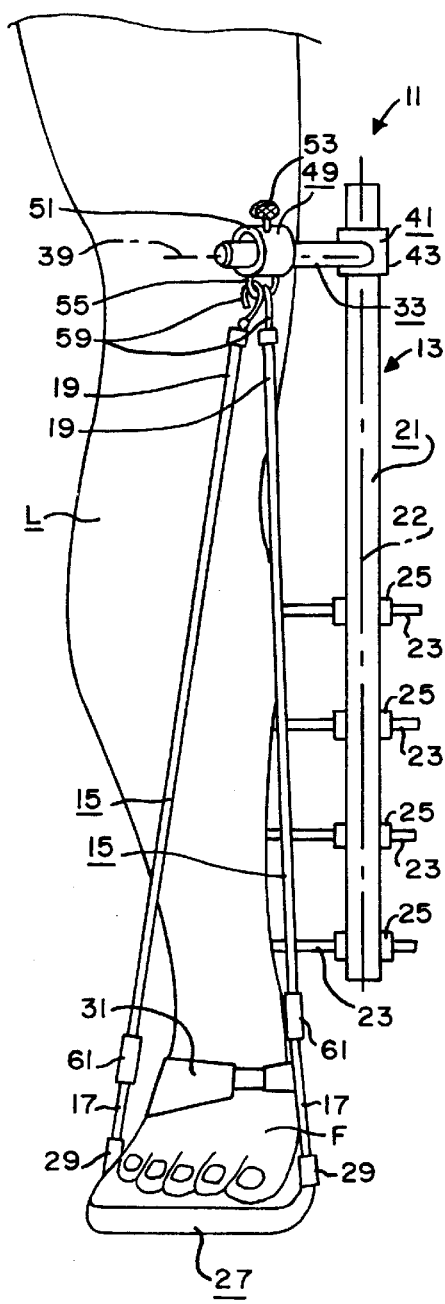

CLAMP DEVICE FOR ORTHOPEDIC EXTERNAL FIXATOR

CROSS-REFERENCE TO RELATED APPLICATIONS

Not Applicable.

STATEMENT RE FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention

The present invention relates, in general, to orthopedic external fixators for use in treating certain bone conditions (e.g., bone fractures) and, more specifically, to means for allowing a strap extending from a patient's foot to be attached to the external fixator.

2. Information Disclosure Statement

Certain boney skeletal injuries or conditions are sometimes treated with an external frame that is attached to the boney skeleton with threaded and/or smooth pins and/or threaded and/or smooth and/or beaded wires. Such constructs are commonly referred to as orthopedic external fixators or external skeletal fixation devices. External fixators may be utilized to treat acute fractures of the skeleton, soft tissue injuries, delayed union of the skeleton when bones are slow to heal, nonunion of the skeleton when bones have not healed, malunion whereby broken or fractured bones have healed in a malposition, congenital deformities whereby bones develop a malposition, and bone lengthening, widening, or twisting.

External fixator frames vary considerably in design and capabilities, and may include multiple or single bars or rods, and a plurality of clamps for adjustably securing the bars to pins or wires which are, in turn, joined to the boney skeleton. The pins or wires may extend completely through the boney skeleton extending out each side of the limb (e.g., transfixation pins) or may extend through the boney skeleton and out one side of the limb (e.g., half pins). Such external fixator frames may be circumferential for encircling a patient's body member (e.g., a patient's tibia), or may be unilateral for extending along one side of a patient's body member. More that one unilateral external fixator frame can be applied to the same length of the patient's body member. Materials for frames also vary, including metals, alloys, plastics, composites, and ceramics.

A circumferential external fixator system was disclosed by G. A. Ilizarov during the early 1950's. The Ilizarov system includes at least two rings or "halos" that encircle a patient's body member (e.g., a patient's leg), connecting rods extending between the two rings, transfixion pins that extend through the patient's boney structure, and connectors for connecting the transfixion pins to the rings.

Mears, U.S. Pat. No. 4,620,533, issued Nov. 4, 1986, discloses a unilateral external fixator system including a plurality of fixation pins attached to at least one rigid bar through adjustable clamps having articulating balls which allow rotational adjustment of each pin or bar.

In order to prevent or avoid foot drop while using an external fixator, straps are sometimes coupled to the patient's foot (e.g., to a post operative surgical shoe or the like worn on the patient's foot) and to one of the pin sites of the external fixator. However, such a method can result in the patient's foot being pulled up at an undesired angle and can result in pin site damage due to the stress put on the pin site by the straps, etc.

A preliminary patentability search conducted in class 602, subclasses 27 and 28, and in class 606, subclasses 53 and 54 produced the following patents which appear to be relevant to the present invention:

McIntyre, U.S. Pat. No. 2,536,454, issued Jan. 2, 1951, discloses a toe lift attachment for leg braces.

Jaquet, U.S. Pat. No. 3,961,854, issued Jun. 8, 1976, discloses an apparatus for orienting and securing a rod in a spatially adjusted position.

Murray, U.S. Pat. No. 4,483,334, issued Nov. 20, 1984, discloses a external fixation device for holding bone segments in known relation to each other.

Pettine, U.S. Pat. No. 4,955,370, issued Sep. 11, 1990, discloses an Achilles tendon rehabilitation brace for protecting motion that may be imposed on a repaired Achilles tendon following surgical anastomosis.

Williamson, U.S. Pat. No. 5,277,699, issued Jan. 11, 1994, discloses a foot drop orthotic and gait training device.

Hess, U.S. Pat. No. 5,542,912, issued Aug. 6, 1996, discloses a foot splint having a back portion, a heel portion, a foot portion, and a diagonally extending frame connecting the heel and foot portions.

Thompson, U.S. Pat. No. 5,860,423, issued Jan. 19, 1999, discloses an ankle-foot orthosis.

Nothing in the known prior art discloses or suggests the present invention. More specifically, nothing in the known prior art discloses or suggests a clamp device for use with an external skeletal fixator for being coupled to a patient's limb, and strap means having a first end for being coupled to a patient's extremity and having a second end. The clamp device includes an elongated clamp rod; a first connection means for adjustably attaching the clamp rod to a fixator rod of the external fixator; and a second connection means for adjustably attaching the second end of the strap means to the clamp rod.

BRIEF SUMMARY OF THE INVENTION

The clamp device of the present invention comprises, in general, an elongated clamp rod; a first connection means for adjustably attaching the clamp rod to a fixator rod of an external fixator; and a second connection means for adjustably attaching the second end of a strap means that is coupled to a patient's extremity to the clamp rod.

BRIEF DESCRIPTION OF THE SEVERAL VIEWS OF THE DRAWINGS

FIG. 1 is a front elevational view of the clamp device of the present invention.

FIG. 2 is a sectional view of the clamp device of the present invention, substantially as taken on line 2—2 of FIG. 1.

FIG. 3 is a sectional view of the clamp device of the present invention, substantially as taken on line 3—3 of FIG. 1.

FIG. 4 is a top plan view of a clamp rod and first connection means construct of the clamp device of the present invention.

FIG. 5 is a front elevational view of the clamp rod and first connection means construct of the clamp device of the present invention.

FIG. 14 is a first side elevational view of a patient's leg and foot, shown combined with an external fixator, a surgical shoe, strap means, and the clamp device of the present invention.

FIG. 15 is a front elevational view of a patient's leg and foot, shown combined with an external fixator, a surgical shoe, strap means, and the clamp device of the present invention.

DETAILED DESCRIPTION OF THE INVENTION

Figure 6:
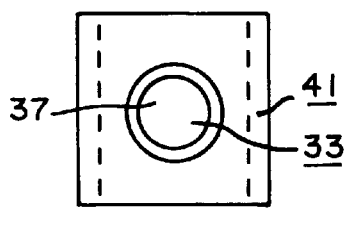
FIG. 6 is a first end elevational view of the clamp rod and first connection means construct of the clamp device of the present invention.
Figure 7:
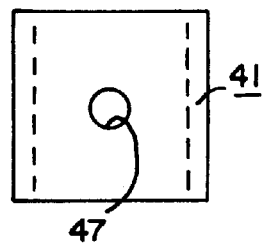
FIG. 7 is a second end elevational view of the clamp rod and first connection means construct of the clamp device of the present invention.
Figure 8:
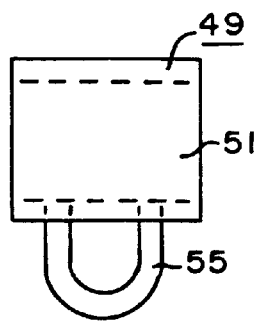
FIG. 8 is a front elevational view of a second connection means of the clamp device of the present invention.
Figure 9:
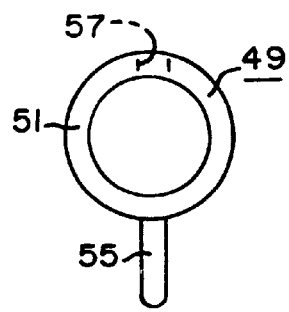
FIG. 9 is an end elevational view of the second connection means of the clamp device of the present invention.
Figure 10:
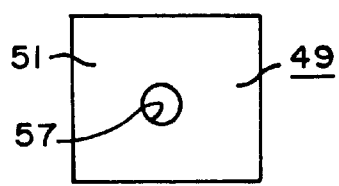
FIG. 10 is a top plan view of the second connection means of the clamp device of the present invention.
Figure 11:
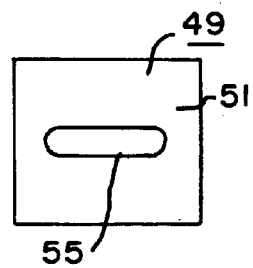
FIG. 11 is a bottom plan view of the second connection means of the clamp device of the present invention.
Figure 12:
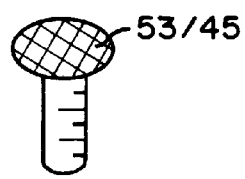
FIG. 12 is a front elevational view of a screw member of the clamp device of the present invention.
Figure 13:
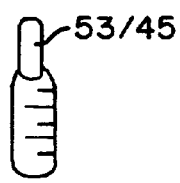
FIG. 13 is a side elevational view of a screw member of the clamp device of the present invention.
Figure 16:
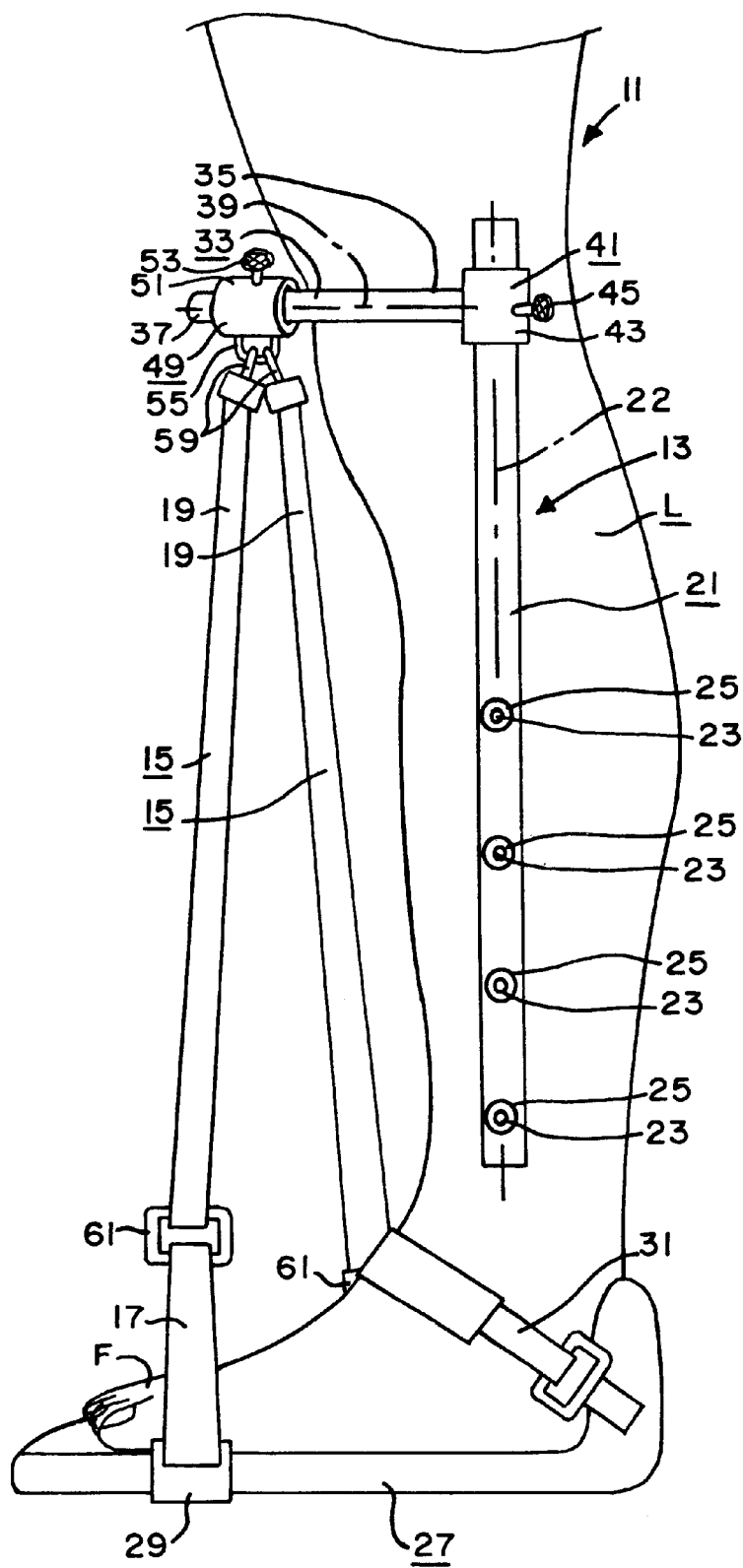
FIG. 16 is a second side elevational view of a patient's leg and foot, shown combined with an external fixator, a surgical shoe, strap means, and the clamp device of the present invention.

A preferred embodiment of the clamp of the present invention is shown in FIGS. 1–16, and identified by the numeral 11. The clamp device 11 for use with an external skeletal fixator 13 for being coupled to a patient's limb (e.g., a patient's leg L), and for use with strap means 15 having a first end 17 for being coupled to a patient's extremity (e.g., the patient's foot F) and a second end 19.

The external fixator 13 may be of any well known type commonly used to treat various skeletal injuries and conditions, and includes at least one elongated, rigid fixator rod 21 having a longitudinal axis 22, a plurality of fixator pins 23 for being joined to the boney skeleton (e.g., on opposite sides of a tibia fracture), and a plurality of connectors 25 for adjustably securing the pins 23 to the rod 21 after the pins 23 are joined to the boney skeleton. While the external fixator 13 may be a circumferential external fixator for encircling a patient's body member, the external fixator 13 shown in the drawings consist of a single unilateral external fixator for extending along one side of a patient's body member.

The clamp device 11 is especially designed for use with a post operative surgical shoe 27 or the like for being worn on the patient's foot F. The surgical shoe 27 preferably has attachment means 29 such as slots or the like for allowing the first end 17 of the strap means 15 to be coupled thereto, and may include tie means 31 or the like for securing the surgical shoe 27 to the patient's foot F.

The clamp device 11 includes an elongated clamp rod 33. The elongated clamp rod 33 has a first end 35, a second end 37, and a longitudinal axis 39 extending between the first and second ends 35, 37 thereof. The clamp rod 33 may be constructed in various manners and out of various materials and in various specific sizes and shapes as will now be apparent to those skilled in the art. Preferably, the clamp rod 33 is constructed as a rigid, one-piece, integral unit out of a standard PVC (polyvinyl chloride) rod, etc., having a 0.5 inch (1.27 centimeter) circular diameter and a 5 inch (12.7 centimeter) length.

The clamp device 11 includes a first connection means 41 for adjustably attaching the clamp rod 33 to the fixator rod 21. The first connection means 41 preferably adjustably attaches the clamp rod 33 to the fixator rod 21 with the longitudinal axis 39 of the clamp rod 33 at an angle to the longitudinal axis 22 of the fixator rod 21. The clamp rod 33 is preferably attached to the fixator rod 21 with the longitudinal axis 39 of the clamp rod 33 at substantially a right angle to the longitudinal axis 22 of the fixator rod 21 as clearly shown in FIGS. 15 and 16. The first connection means 41 preferably incudes a first connection sleeve member 43 for encircling the fixator rod 21. The first connection sleeve member 43 is preferably fixedly and permanently attached to the first end 35 of the clamp rod 33. The first connection sleeve member 43 may be constructed in various manners and out of various materials and in various specific sizes and shapes as will now be apparent to those skilled in the art. Preferably, the first connection sleeve member 43 is constructed as a rigid, one-piece, integral unit out of a standard schedule 40 PVC (polyvinyl chloride) pipe, etc., having a 0.75 inch (1.905 centimeter) outside diameter and a 1 inch (2.54 centimeter) length. The first connection sleeve member 43 is preferably fixedly attached to the first end 35 of the clamp rod 33 by, for example, being glued thereto. Alternatively, the first connection sleeve member 43 and clamp rod 33 could be constructed as a one-piece, integral unit out of plastic, metal or other substantially strong, rigid material. The first connection means 41 preferably includes a screw member 45 for extending through the first connection sleeve member 43 and against the fixator rod 21 to fixedly secure the first connection sleeve member 43 to the fixator rod 21. The screw member 45 preferably consist of an off-the-shelf ³⁄₁₆ inch (0.47625 centimeter) by ½ inch (1.27 centimeter) thumb screw or the like. The first connection sleeve member 43 preferably has a threaded aperture 47 therethrough for screwably receiving the screw member 45.

The clamp device 11 includes a second connection means 49 for adjustably attaching the second end 19 of the strap means 15 to the clamp rod 33. The second connection means 49 preferably includes a second connection sleeve member 51 for encircling the clamp rod 33, a screw member 53 for extending through the second connection sleeve member 51 and against the clamp rod 33 as clearly shown in FIG. 2 to fixedly secure the second connection sleeve member 49 to the clamp rod 33, and a bracket 55 attached to the second connection sleeve member 51 for allowing the second end 19 of the strap means 15 to be attached to the second connection means 49 as clearly shown in FIGS. 14–16. The bracket 55 of the second connection means 49 is preferably U-shaped. The second connection sleeve member 49 may be constructed in various manners and out of various materials and in various specific sizes and shapes as will now be apparent to those skilled in the art. Preferably, the second connection sleeve member 51 is constructed as a rigid, one-piece, integral unit out of a standard schedule 40 PVC (polyvinyl chloride) pipe, etc., having a 0.5 inch (1.27 centimeter) outside diameter and a 1 inch (2.54 centimeter) length. The second connection sleeve member 51 is preferably fixedly attached to the bracket 55 by, for example, being bolted (via standard nuts, not shown) or glued thereto. The bracket 55 may consist of an off-the-shelf ⅛ inch (0.3175 centimeter) U-bolt. Alternatively, the second connection sleeve member 51 and bracket 55 could be constructed as a one-piece, integral unit out of plastic, metal or other substantially strong, rigid material. The screw member 51 preferably consist of an off-the-shelf 3/16 inch (0.47625 centimeter) by ½ inch (1.27 centimeter) thumb screw or the like. The second connection sleeve member 51 preferably has a threaded aperture 57 therethrough for screwably receiving the screw member 53.

As hereinabove discussed, the clamp device 11 of the present invention is designed primarily for patients having an external fixator 13 including a fixator rod 21 and a plurality of fixator pins 23 attached a leg. Typically, the patient will wear a surgical shoe 27 having the first end 17 of strap means 15 (e.g., a pair of strap members) attached thereto. Prior to the present invention, in order to prevent or avoid foot drop, etc., the second end 19 of the strap means 15 would be tied or otherwise secured to one of the fixator pins 23. While such a method would prevent or avoid foot drop, it also put stress on the pin site, often resulting in damage to the pin site, and, because the location of the fixator pins 23 were not adjustable, sometimes caused the patient's foot F to be pulled up at an undesired angle. To use the clamp device 11 with such an external fixator 13, the first connection sleeve member 43 is merely slid over one end of the fixator rod 21. Both the clamp rod 33 and the second connection means 49 can be adjusted (moved up and down on the fixator 21 and back and forth on the clamp rod 33) to position the bracket 55 at the desired location to position the patient's foot F at the desired angle (e.g., substantially at right angles to the longitudinal axis of the patient's leg L as clearly shown in FIGS. 14 and 16). Once the desired location is found, the screw members 45, 53 are tightened to lock and secure the clamp rod 33 and second connection means 49 in place. The second ends 19 of the strap means 15 can then be attached to the bracket 55. Preferably, the strap means 15 will include hooks or snaps 59 on the second ends 19 thereof for allowing easy and fast connection to the bracket 55, and length adjustment means 61 such as typical buckles or the like for allowing the strap means 15 to be easily adjusted to the desired overall length. As will now be apparent, the angle of the patient's foot F can be varied by changing the overall length of the strap means 15 and/or the location of the bracket 55.

Although the present invention has been described and illustrated with respect to a preferred embodiment and a preferred use therefor, it is not to be so limited since modifications and changes can be made therein which are within the full intended scope of the invention.

What is claimed is:

1. A clamp device for use with an external skeletal fixator for being coupled to a patient's limb, and strap means having a first end for being coupled to a patient's extremity and having a second end; the external skeletal fixator including an fixator rod and a plurality of fixator pins; said clamp device comprising:
   (a) an elongated clamp rod;
   (b) a first connection means for adjustably attaching said clamp rod to a fixator rod of an external skeletal fixator; and
   (c) a second connection means for adjustably attaching the second end of a strap means to said clamp rod.

2. The clamp device of claim 1 in which the fixator rod has a longitudinal axis; in which said clamp rod has a longitudinal axis; and in which said first connection means is for adjustably attaching said clamp rod to the fixator rod with said longitudinal axis of said clamp rod at an angle to the longitudinal axis of the fixator rod.

3. The clamp device of claim 1 in which the fixator rod has a longitudinal axis; in which said clamp rod has a longitudinal axis; and in which said first connection means is for adjustably attaching said clamp rod to the fixator rod with said longitudinal axis of said clamp rod at substantially a right angle to the longitudinal axis of the fixator rod.

4. The clamp device of claim 1 in which said first connection means incudes a first connection sleeve member for encircling the fixator rod.

5. The clamp device of claim 4 in which said first connection means includes a screw member for extending through said first connection sleeve member and against the fixator rod for fixedly securing said first connection sleeve member to the fixator rod.

6. The clamp device of claim 1 in which said second connection means includes a second connection sleeve member for encircling said clamp rod.

7. The clamp device of claim 6 in which said second connection means includes a screw member for extending through said second connection sleeve member and against said clamp rod to fixedly secure said second connection sleeve member to said clamp rod.

8. The clamp device of claim 6 in which said second connection means includes a bracket attached to said second connection sleeve member for allowing the second end of the strap means to be attached to said second connection means.

9. The clamp device of claim 8 in which said bracket of said second connection means is U-shaped.

10. A clamp device for use with an external skeletal fixator, a post operative surgical shoe, and strap means having a first end for being attached to the shoe and having a second end; the external skeletal fixator including an fixator rod having a longitudinal axis and including a plurality of fixator pins for being connected to the fixator rod and joined to boney skeleton; said clamp device comprising:
   (a) an elongated clamp rod having a longitudinal axis;
   (b) a first connection means for adjustably attaching said clamp rod to a fixator rod of an external skeletal fixator with said longitudinal axis of said clamp rod at substantially a right angle to the longitudinal axis of the fixator rod; said first connection means including a first connection sleeve member for encircling the fixator rod and a screw member for extending through said first connection sleeve member and against the fixator rod for fixedly securing said first connection sleeve member to the fixator rod; and
   (c) a second connection means for adjustably attaching the second end of a strap means to said clamp rod; said second connection means including a second connection sleeve member for encircling said clamp rod, a screw member for extending through said second connection sleeve member and against said clamp rod to fixedly secure said second connection sleeve member to said clamp rod, and a bracket attached to said second connection sleeve member for allowing the second end of the strap means to be attached to said second connection means.

* * * * *